United States Patent [19]
Harvey et al.

[11] Patent Number: 5,939,259
[45] Date of Patent: Aug. 17, 1999

[54] METHODS AND DEVICES FOR COLLECTING AND STORING CLINICAL SAMPLES FOR GENETIC ANALYSIS

[75] Inventors: Michael A. Harvey, Spofford; Richard D. Kremer, Keene; Robert L. Burghoff, Westmoreland, all of N.H.; Thomas H. King, Brattleboro, Vt.

[73] Assignee: Schleicher & Schuell, Inc., Keene, N.H.

[21] Appl. No.: 08/835,614

[22] Filed: Apr. 9, 1997

[51] Int. Cl.⁶ .................. C12Q 1/68; C07K 1/00; C12N 1/08; C07H 21/02
[52] U.S. Cl. .................. 435/6; 435/269; 435/270; 536/25.42
[58] Field of Search .................. 435/89, 91.1, 270, 435/6, 91.2, 269, 278; 424/488, 443, 464; 536/25.4, 25.41, 25.42

[56] References Cited

U.S. PATENT DOCUMENTS

| | | | |
|---|---|---|---|
| 5,234,809 | 8/1993 | Boom et al. | 435/91.2 |
| 5,496,562 | 3/1996 | Burgoyne | 424/488 |
| 5,501,963 | 3/1996 | Burckhardt | 435/91.2 |

OTHER PUBLICATIONS

Harvey et al. "Impregnated 903(TM) Blood Collection Oaoer: A Tool for DNA Prepartion from Dried Blood Spots for PCR Amplification", Clin. Chem. (1995) 41(6): S108.

Primary Examiner—Jean C. Witz
Assistant Examiner—Susan Hanley
Attorney, Agent, or Firm—Brian D. Voyce

[57] ABSTRACT

The present invention relates to devices and methods for the collection, storage, and purification of nucleic acids, such as DNA or RNA, from fluid samples for subsequent genetic characterization, primarily by conventional amplification methods. The present invention can be used to collect, store, or purify nucleic acids from a treated whole blood source that has naturally occurring nucleic acid amplification inhibitors present, as well as added blood stabilization components that also inhibit nucleic acid amplification. More importantly, these nucleic acids can be released after collection or storage in a manner that enables them to be amplified by conventional techniques such as polymerase chain reaction. In particular, an absorbent material that does not bind nucleic acids irreversibly is impregnated with a chaotropic salt. A biological source sample is contacted with the impregnated absorbent material. Any nucleic acids present in the biological source can be either eluted or resolubilized off the absorbent material.

12 Claims, 7 Drawing Sheets

METHODS AND DEVICES FOR COLLECTING AND STORING CLINICAL SAMPLES FOR GENETIC ANALYSIS

TECHNICAL FIELD

The present invention relates to devices and methods for the collection, storage, and purification of nucleic acids, such as DNA or RNA, from fluid samples for subsequent genetic characterization, primarily by conventional amplification methods. The present invention can be used to collect, store, or purify nucleic acids either from a biological source other than untreated whole blood, the biological source having naturally occurring nucleic acid amplification inhibitors present, (including either a buccal swab, cerebrospinal fluid, feces, lymphatic fluid, a plasma sample, a saliva sample, a serum sample, urine, or a suspension of cells or viruses), or from a treated whole blood source that has naturally occurring nucleic acid amplification inhibitors present, as well as added blood stabilization components that also inhibit nucleic acid amplification. More importantly, these nucleic acids can be released after collection or storage in a manner that enables them to be amplified by conventional techniques such as polymerase chain reaction. In particular, an absorbent material that does not bind nucleic acids irreversibly is impregnated with a chaotropic salt. A biological source sample is contacted with the impregnated absorbent material. Any nucleic acids present in the biological source can be either eluted or resolubilized off the absorbent material.

BACKGROUND ART

The collection and storage of biological fluids, such as blood, is well represented by neonatal testing of infants for phenylketourionic acid (PKU). The heel of a newborn child is pricked by a lance. A piece of cellulose paper is applied to the blood spot. The spot is allowed to dry before being sent to a laboratory for testing. Almost all of the neonatal testing for PKU is performed in this manner. However, such a technique is not easily applicable to the collection and storage of biologically related fluids when one desires to analyze any nucleic acids present in the biological source. One would have to use a protease digestion, organic extraction, and/or an ion exchange step in order to retrieve nucleic acids.

Nucleic acids, such as deoxyribonucleic acids (DNA) or ribonucleic acids (RNA), have become of increasing interest as analytes for clinical or forensic uses. Powerful new molecular biology technologies enable one to detect for congenital diseases or infectious diseases. These same technologies can characterize DNA for use in settling factual issues in legal proceedings such as paternity suits and criminal prosecutions. Nucleic acid testing has been made possible due to powerful amplification methods. One can take small amounts of nucleic acids which, in and of themselves would be undetectable, and increase or amplify the amount to a degree where useful amounts are present for detection.

The most commonly employed amplification technique is known as polymerase chain reaction, (PCR). Nucleic acid polymerases are used with template DNA from the sample in a cycled manner to create greater amounts of a starting nucleic acid materials, which are easily detected. One of ordinary skill in the art knows that the effectiveness and reproducibility of PCR amplification is dependent, in part, on the purity and amount of the DNA template. Certain molecules present in biological sources of nucleic acids are known to stop or inhibit PCR amplification. For example, in whole blood, hemoglobin is known to inhibit PCR reactions. Thus, the removal or inactivation of such inhibitors is a key factor in performing PCR reactions.

A method for storing DNA is disclosed in U.S. Pat. No. 5,496,562 to Leigh A. Burgoyne. An absorbent cellulose based matrix is treated with a combination of a weak base, a chelating agent, an anionic detergent, and, optionally, uric acid. The resulting product has an alkaline pH. DNA binds to this matrix and is protected against degradation.

A process for isolating nucleic acids is shown in U.S. Pat. No. 5,234,809 to William R. Boom et alia, (Boom). Recognizing that typical biological sources of nucleic acids can affect PCR reactions, Boom discloses using a combination of a biological source material, chaotropic salt, and a solid support, preferably finely divided glass. All three elements are combined in a liquid mixing device, with any nucleid acids present binding to the glass. After mixing, the solid support must be removed from the mixing device, washed, and the template nucleic acid eluted. Only then can it be exposed to amplification reactions.

Chaotropic salts have been used in association with isolating RNA. U.S. Pat. No. 4,483,920 to David Gillespie et alia, discloses a method for immobilizing messenger RNA onto filter material. Cellular components are solubilized using a chaotropic salt. The solubilized components are then passed through a filter, the messenger RNA selectively binding to the filter. The filter and RNA are baked prior to measurement by a labeled probe. Another method is shown by David Gillespie et alia, in U.S. Pat. No. 5,155,018. Here, RNA-containing sources are contacted with finely-divided glass in the presence of a binding solution comprising concentrated, acidified chaotropic salts. Under these conditions, RNA, but not DNA, binds selectively to the glass.

A poster disclosure at the annual American Association of Clinical Chemistry in 1995 by Dr. Michael A. Harvey et alia revealed that chaotropic salts can be used to prepare DNA from dried and untreated whole blood spots for PCR amplification. Hemoglobin present in dried untreated whole blood spots was known to cause an inhibition of PCR reactions. A cellulosic paper treated with a chaotropic salt was found to overcome the problem of hemoglobin inhibition in untreated whole blood spots.

DISCLOSURE OF THE INVENTION

The present invention relates to devices and methods for the collection, storage, and purification of nucleic acids, such as DNA or RNA, from fluid samples for subsequent genetic characterization, primarily by conventional amplification methods. The present invention can be used to collect, store, or purify nucleic acids either from a biological source other than untreated whole blood, the biological source having naturally occurring nucleic acid amplification inhibitors present other than hemoglobin, (including samples from either a buccal swab, cerebrospinal fluid, feces, lymphatic fluid, a plasma sample, a saliva sample, a serum sample, urine, or a suspension of cells or viruses) or from a treated whole blood source that has naturally occurring nucleic acid amplification inhibitors present, as well as added blood stabilization components that also inhibit nucleic acid amplification.

For example, the present invention can be used to detect pathogens such as bacteria or viruses that can be found in the circulatory system. More importantly, these nucleic acids can be released after collection or storage in a manner that enables them to be amplified by conventional techniques such as polymerase chain reaction. The release of amplifiable nucleic acids is substantially more than in the presence of the inhibitory composition alone. In particular, an absorbent material that does not bind nucleic acids irreversibly is impregnated with a chaotropic salt. A biological source sample is contacted with the impregnated absorbent material and dried. Any nucleic acids present in the biological source can be either eluted or re-solubilized off the absorbent material. The present device can collect nucleic acids not only from point sources such as humans or animals, but also can be used to collect widely disseminated sources such as fungal spores, viruses, or bacterial spores, or bodily fluids present at crime scenes.

The present device for collecting, purifying, and storing nucleic acids from biological sources comprises an absorbent material that does not bind to nucleic acids and a chaotropic salt impregnated about the absorbent material. (For the purposes of the present invention, "chaotropic salts" include any substance capable of altering the secondary, tertiary, or quaternary structure of biomolecules in aqueous solution, but leaves the primary structure intact.) Preferably, a chaotropic salt should inactivate any nucleic acid amplification inhibitors present in the biological source, by precipitation, by inducing the inhibitor to irreversibly bind to the matrix, or by causing substantially irreversible denaturation of the inhibitor. Suitable chaotropic salts include guanidinium salts such as guanidine isothiocyanate, guanidine thiocyanate, guanidine hydrochloride, sodium iodide, sodium perchlorate, potassium iodide, sodium (iso) thiocyanate, urea, or combinations thereof. The salts can be impregnated about the absorbent material by contacting the absorbent material with a solution containing the chaotropic salt. Such solutions can contain from about 0.1M to 6.0M salt concentrations, preferably 0.5M to 2.0M. The absorbent material is then dried.

Many materials are suitable as the absorbent material. The main characteristics needed for the absorbent material are that it is or can be made hydrophilic, bibulous, and does not substantially bind nucleic acids irreversibly through either hydrophobic, ionic, covalent, or electrostatic means. The matrix must not by itself inhibit or bind amplification reactants, release substances that effect amplification reactants or otherwise affect PCR and other amplification reactions. Suitable materials include cellulosics, woven porous polymers, or non-woven porous polymers, including polyesters and polypropylenes.

Common inhibitors to nucleic acid amplification can be present naturally in a biological source or can be added for handling or processing of a sample from a biological source, (Gunnar Tasa et alia, 1995, *Methods in Molecular and Cellular Biology;* 5, 122–124). Naturally occurring chelating molecules, enzymes and proteins can damage either nucleic acid templates, (such as RNAses, DNAses), or damage PCR polymerases used in the amplification reactions, (such as proteases). These substances can be found in buccal swabs, cerebrospinal fluids, feces, lymphatic fluids, plasma, saliva, serum, sputum, or urine. In addition, components added to whole blood samples can interfere with nucleic acid amplification reactions. Examples of such components used to treat whole blood include anticoagulants, such as heparin, or chelators, such as EDTA or citrate anion.

BEST MODES FOR CARRYING OUT THE INVENTION

Figure 1:
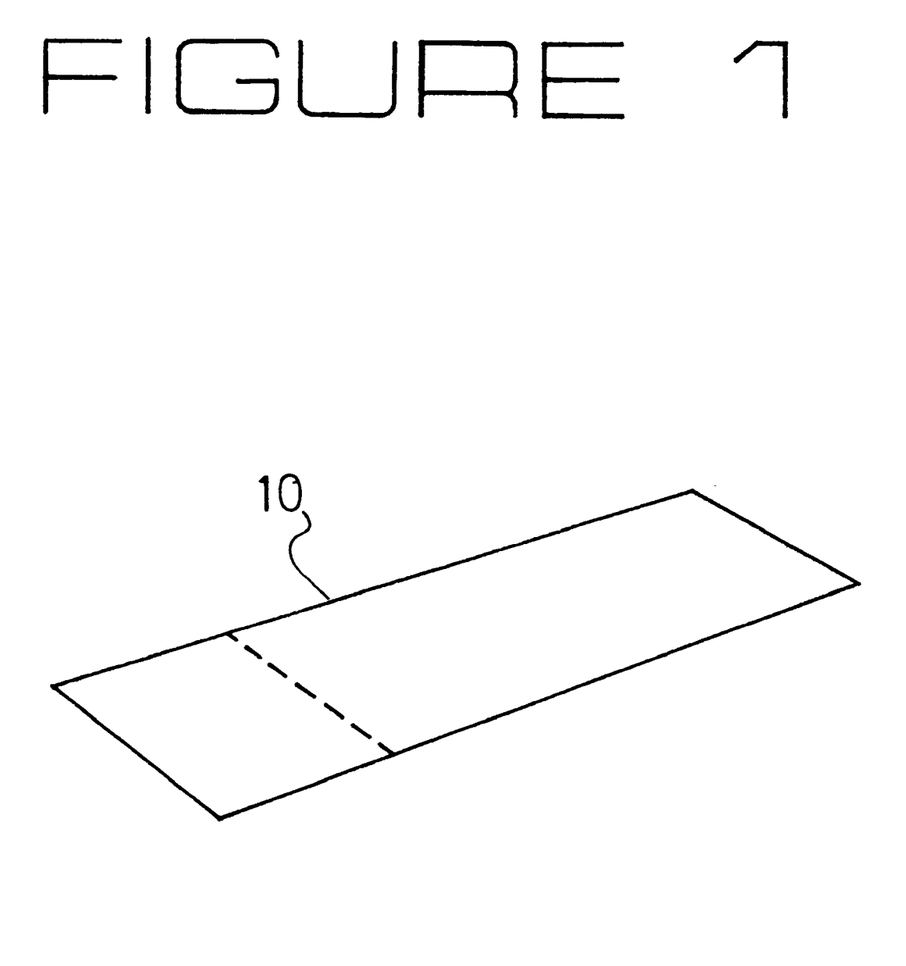
FIG. 1 is an isometric view of a preferred flat sheet embodiment of the device.
Figure 2:
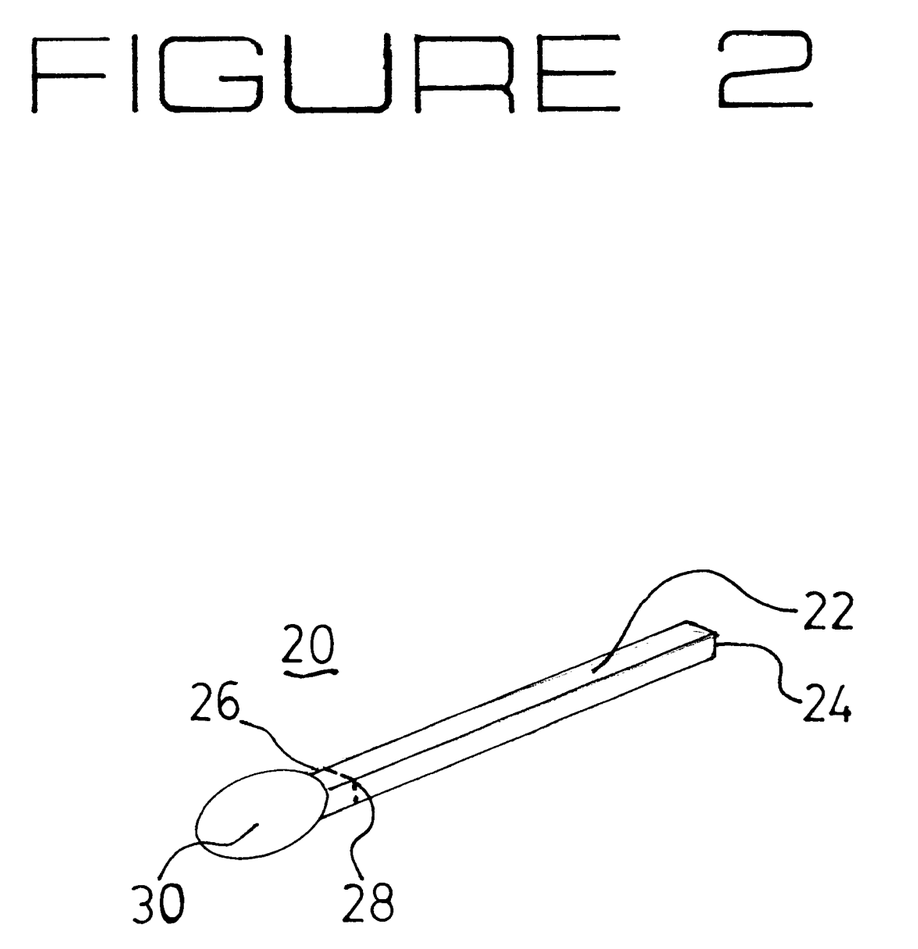
FIG. 2 is an isometric view of a preferred ovoid embodiment of the device.

Preferred embodiments of the present invention use cellulosics, in particular, flat sheet paper as an absorbent material. The shape or configuration of the absorbent material can vary. One can choose from flat sheets or spherical shapes. For example, FIG. 1 shows a flat sheet device (10) having a ready made perforation lines (12). One can simply contact the sheet with a biological source fluid or tissue and break off a piece of the absorbent material at the perforation. (Alternatively, FIG. 2 shows a ovoid dip device (20), shaped much like a match stick.) The device comprises three elements. The first is a handle means (22) that has a distal end (24) and a proximal end (26). The distal end is easily separable manually from the handle end. This can be achieved either by a perforation or a scribing (28) that weakens the connection to the handle. Absorbent material (30) that does not bind to nucleic acids is disposed about the distal end of the handle means. Finally, a chaotropic salt is impregnated about the absorbent material by dipping the absorbent material into a solution containing from 0.5M to 2.0M chaotropic salt, such as guanidine (iso)thiocyanate. The absorbent material is then dried. In use, one holds the proximal end (26) and contacts the distal absorbent head (24) with the biological source.

Cellulosic papers are suitable for the present invention. A representative, commercially available paper is known as "903 Blood Collection Paper" and is made by Schleicher & Schuell, Inc., of Keene, N.H. The characteristics of this cellulosic paper are as follows:

| Liquid Filtration Speed | Densometer | Retained Precipitates |
|---|---|---|
| TAPPI T471 u.m. 572 ASTM E832-9.3 (7.3 seconds) | TAPPI T471 u.m. 572 ASTM 726 (20 seconds) | ASTM D981-56 (8 to 30 μm particles) |
| Surface | Basis Weight | Caliper |
| smooth, not hardened | TAPPI T471 u.m.572 TAPPI T410 ASTM 646 (179 g/m$^2$) | TAPPI T471 u.m. 572 TAPPI T411 ASTM 643 (0.52 mm thick) |
| Water Absorbency | Klemm | Wet Strength -5 sheets |
| TAPPI T441 ASTM 3285 (4.5 g/100 cc) | TAPPI T441 ASTM 3285 (34/16"/min) | TAPPI T471 ASTM 774 (7.0 psi) |

Other suitable paper is known to those of ordinary skill in the art, such as Whatman 3MM or BFC1 80 (of Fairfield, N.J.), or Schleicher & Schuell, Inc. GB002, GB003, GB004 and other common filter papers.

Other reagents can be added to the present invention in order to enhance lysis or disruption of intact cells, bacteria or viruses absorbed onto the device. For example, suitable anionic, cationic, or zwitterionic surfactants, such as Tween 20 or Triton X-100, can be impregnated into the absorbent material along with the chaotropic salt. Suitable concentrations for chaotropic salts range from 0.005 wt. % to 5 wt. %. Conventional pH buffers can be made from sodium phosphate or Tris in order to maintain a desired pH level

EXAMPLE 1

Fabrication Of Absorbent Material

A roll of 903 paper is impregnated with a guanidine thiocyanate solution having a concentration of between 0.5M and 5.0M, preferably about 2.0M. The paper is immersed into a bath of the guanidine thiocyanate solution, sent through a drying tunnel and allowed to dry at 80° C. for about 20 to 30 minutes. The dried paper is rolled up for further processing. One can make predetermined flat shapes of absorbent material by either cutting or punching, which are known to those of skill in the art.

EXAMPLE 2

Use Of Device With A Fecal Source

Two separate one inch squares of 903 paper were exposed to replicate human fecal samples containing nucleic acids. One was untreated 903 paper, the other was treated as set forth in Example 1. The fecal matter was allowed to dry. Two one eighth inch circles of dried fecal matter spot were hand punched from the sheet in each. Each punch was transferred to a first 1.5 ml centrifuge tube containing 0.5 ml of water and vortexed for about 5 seconds. The punches were then transferred to a second 1.5 ml centrifuge tube containing 100 $\mu$l of water and placed in a heating block at 95° C. for about 30 minutes.

Figure 3:
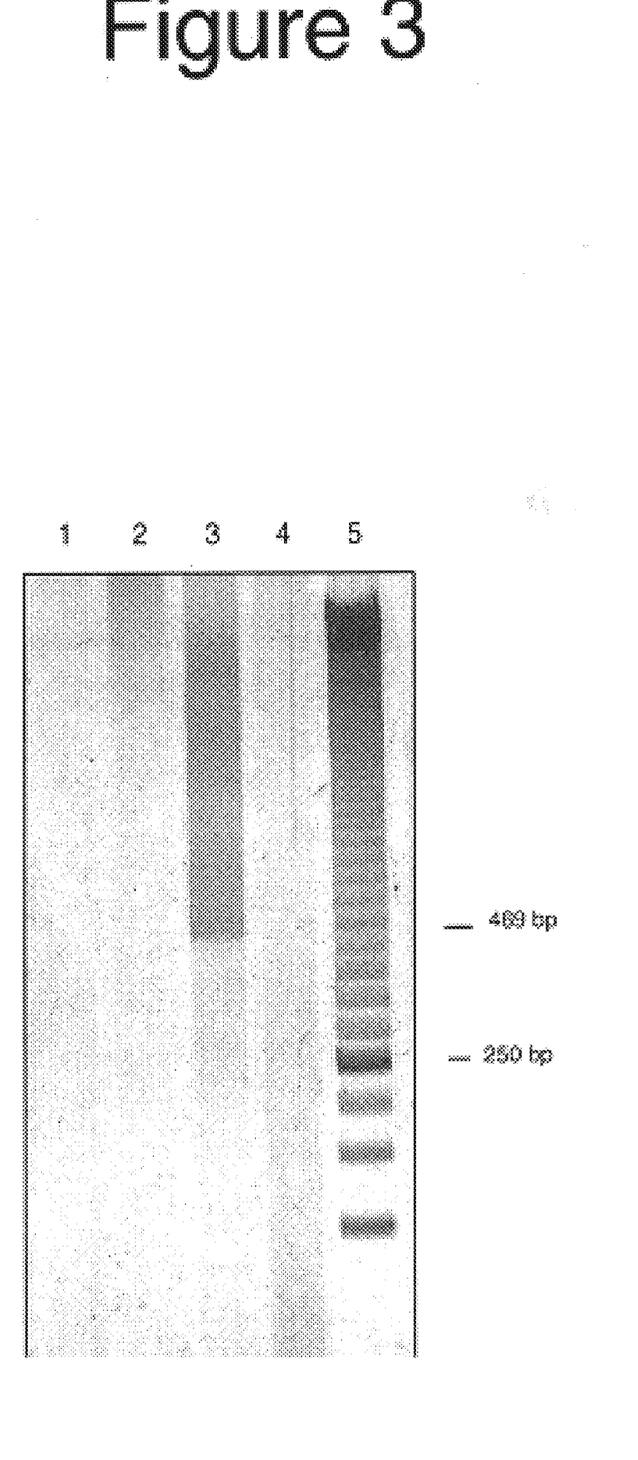
FIG. 3 is a view of an electrophoretic gel as described in Example 2.

Ten $\mu$l of supernatant from each sample was transferred to a PCR reaction mixture containing primers to amplify DNA coding for the genes for bacterial 16S ribosomal RNA. Amplification was allowed to proceed for 35 cycles. The amplified products were analyzed by electrophoresis on a polyacylamide gel which were visualized by silver staining. As shown in FIG. 3, the gel patterns demonstrated that PCR reactions using DNA templates from samples collected on untreated 903 paper generated little detectable PCR product, while those from samples collected on the present invention yielded a strong band indicating a successful PCR reaction. Lanes 1 to 5 in FIG. 3 are differentiated as follows: lane 1 has only untreated 903 paper; lane 2 has a 10 $\mu$l elution of fecal material on untreated 903 paper; lane 3 has a 10 $\mu$l elution on treated 903 paper; lane 4 is treated 903 paper alone; and lane 5 shows a 50 base pair ladder.

EXAMPLE 3

Use Of Device With A Saliva Source

Two separate one inch squares of 903 paper or the present invention are exposed to replicate human saliva samples containing nucleic acids. The saliva was allowed to dry. One was untreated 903 paper, the other was treated as set forth in Example 1. Two one eighth inch circles of dried saliva spots were hand punched from the sheet in each. Each punch was transferred to a first 1.5 ml centrifuge tube containing 0.5 ml of water and vortexed for about 5 seconds. The punches were then each transferred to a second 1.5 ml centrifuge tube containing 100 $\mu$l of water and preferably placed in a heating block at 95 ° C. for about 30 minutes.

Figure 4:
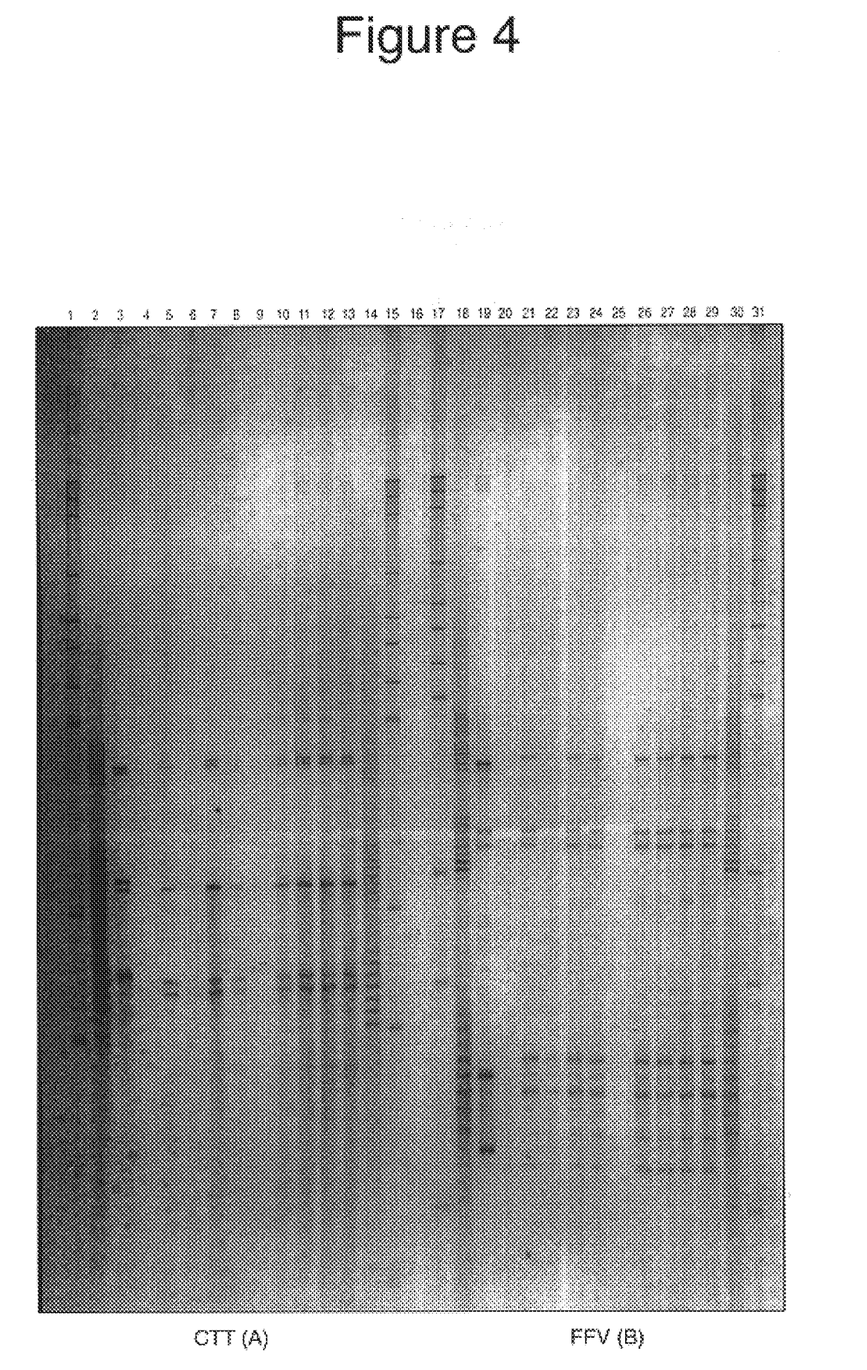
FIG. 4 is a view of an electrophoretic gel as described in Example 3.

Ten $\mu$l of supernatant from each was transferred to a PCR reaction mixture containing primers specific various short tandem repeats. Amplification was allowed to proceed for 35 cycles. The amplified products were analyzed by electrophoresis on a polyacylamide gel which were visualized by silver staining. As shown in FIG. 4, the gel patterns demonstrated that PCR reactions using DNA templates from untreated 903 paper generated detectable PCR product, however those from the present invention yields a much stronger band indicating a successful PCR reaction that was about 5–10 times more productive. The lanes in FIG. 4 can be differentiated as follows: lanes 1, 5, 17, and 31 used pGEM molecular weight markers from Promega Corp. of Madison, Wis.; lanes 2 and 14 are CTT (also from Promega Corp.) multiplex ladders; lanes 3 and 19 used 25 nanograms of K562 DNA; lanes 4 and 20 are untreated 903 paper runs; lanes 5 to 8 and 21 to 24 used saliva samples on untreated 903 paper; lanes 9 and 25 are treated 903 paper runs; lanes 10 to 13 and 27 to 30 used saliva samples on treated 903 paper.

EXAMPLE 4

Alternative Use Of Device With A Saliva Source

Two separate one inch squares of 903 paper are exposed to replicate human saliva samples containing nucleic acids. One was untreated 903 paper, the other was treated as set forth in Example 1. The saliva was allowed to dry. Two one eighth inch circles of dried saliva spot were hand punched from the sheet in each. Each punch was transferred to a 1.5 ml microcentrifuge tube containing 0.5 ml of water, and the tube vortexed for about 5 seconds.

Figure 5:
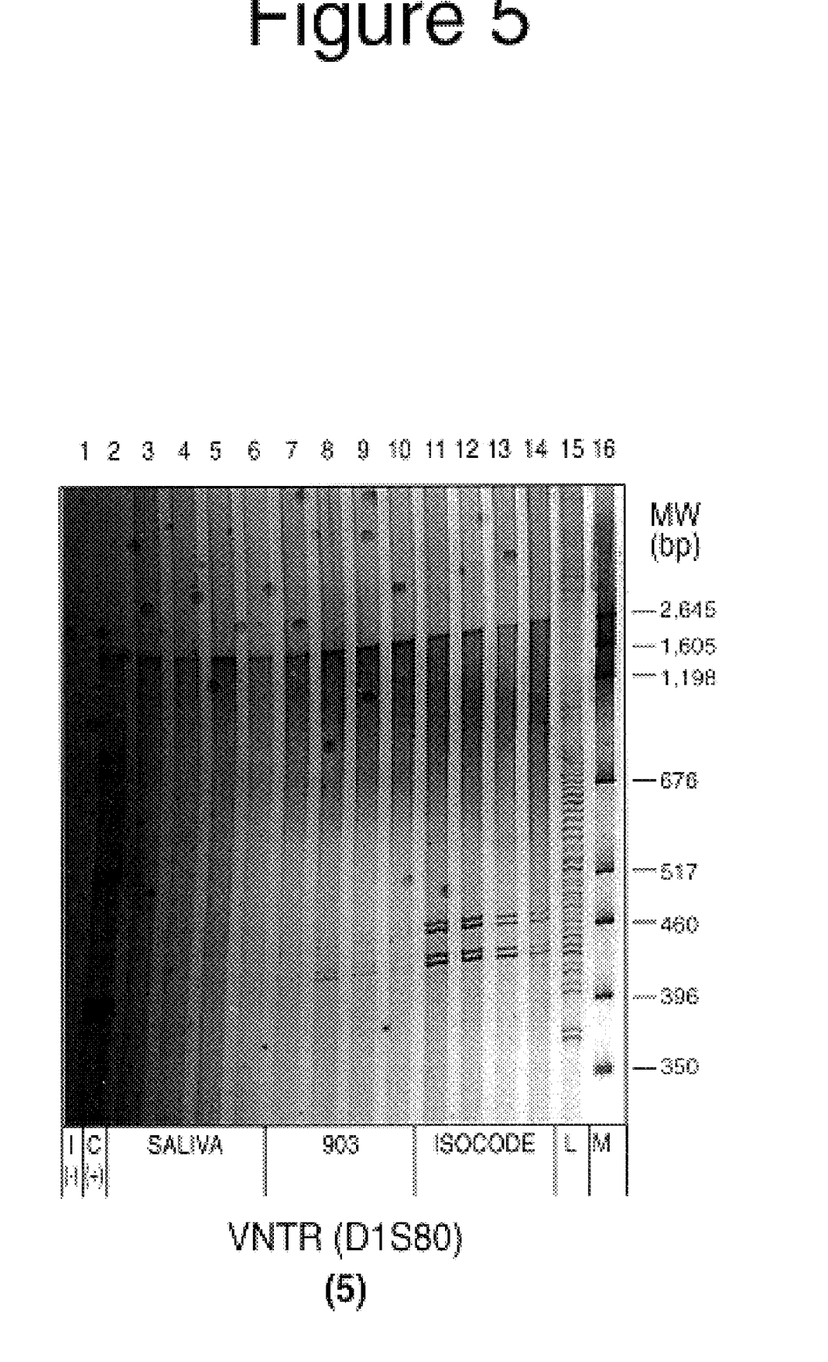
FIG. 5 is a view of an electrophoretic gel as described in Example 4.

Unlike in Example 3, the punches were then each transferred directly into a PCR reaction mixture containing primers specific for the VNTR DS180 locus. Amplification was allowed to proceed for 30 cycles. The amplified products were analyzed by electrophoresis on a polyacylamide gel which were stained by silver staining. As shown in FIG. 5, the gel patterns demonstrated that PCR reactions using DNA templates from untreated 903 paper generated detectable PCR product, however those from the present invention yielded a much strong band indicating a successful PCR reaction that was about 5 to 10 times more productive. The lanes in FIG. 5 can be differentiated as follows: lane 1 is a treated 903 paper control; lane 2 used 25 nanograms of K562 DNA; lanes 3 to 6 used D1S80 from saliva; lanes 7 to 10 used D1S80 from untreated 903 paper; lanes 11 to 14 used D1S80 from treated 903 paper; lane 15 is a Gene Print™ allelic ladder from Perkin Elmer Corporation; and lane 16 used pGEM molecular weight marker.

EXAMPLE 5

Use Of Device For Multiplexing From A Saliva Source

Two separate one inch squares of 903 paper are exposed to replicate human saliva samples containing nucleic acids. One was untreated 903 paper, the other was treated as set forth in Example 1. The saliva was allowed to dry. Two one eighth inch circles of dried saliva spot were hand punched from the sheet in each. Each punch was transferred to a 1.5 ml microcentrifuge tube containing 0.5 ml of water, and the tube vortexed for about 5 seconds.

Figure 6:
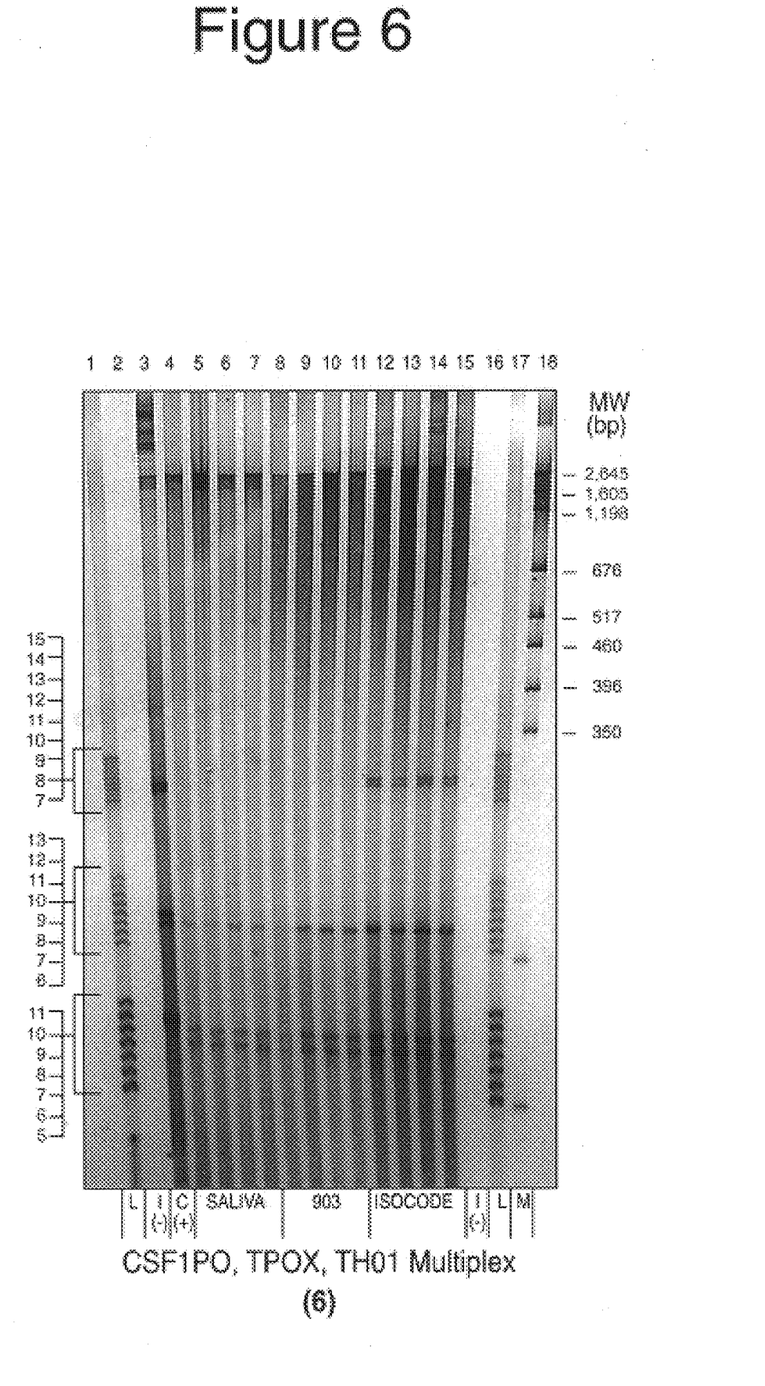
FIG. 6 is a view of an electrophoretic gel as described in Example 5.

Saliva template DNA from the above samples was used in a multiplexed amplification of short tandem repeats (STR), amplification of samples from untreated 903 paper generated detectable PCR products for only 2 of 3 loci. As shown by an electrophoretic gel result in FIG. 6, samples from the present invention generated detectable products for all three loci of the multiplex that were five to ten times more abundant. It should be noted that if fresh, undried saliva is added to a PCR reaction only two of three loci present are amplified. The lanes in FIG. 6 can be differentiated as follows: lanes 1 and 17 are CTT multiplex ladders; lane 2 is untreated 903 paper; lane3 used 25 nanograms of K562 DNA; lanes 4 to 7 are CTT from saliva; lanes 8 to 11 are CTT from untreated 903 paper; lanes 12 to 15 are CTT from treated 903 paper; lane 16 is treated 903 paper; and lane 18 used a pGEM molecular weight marker.

EXAMPLE 6

Use Of Device With A Treated Whole Blood Source

Figure 7:
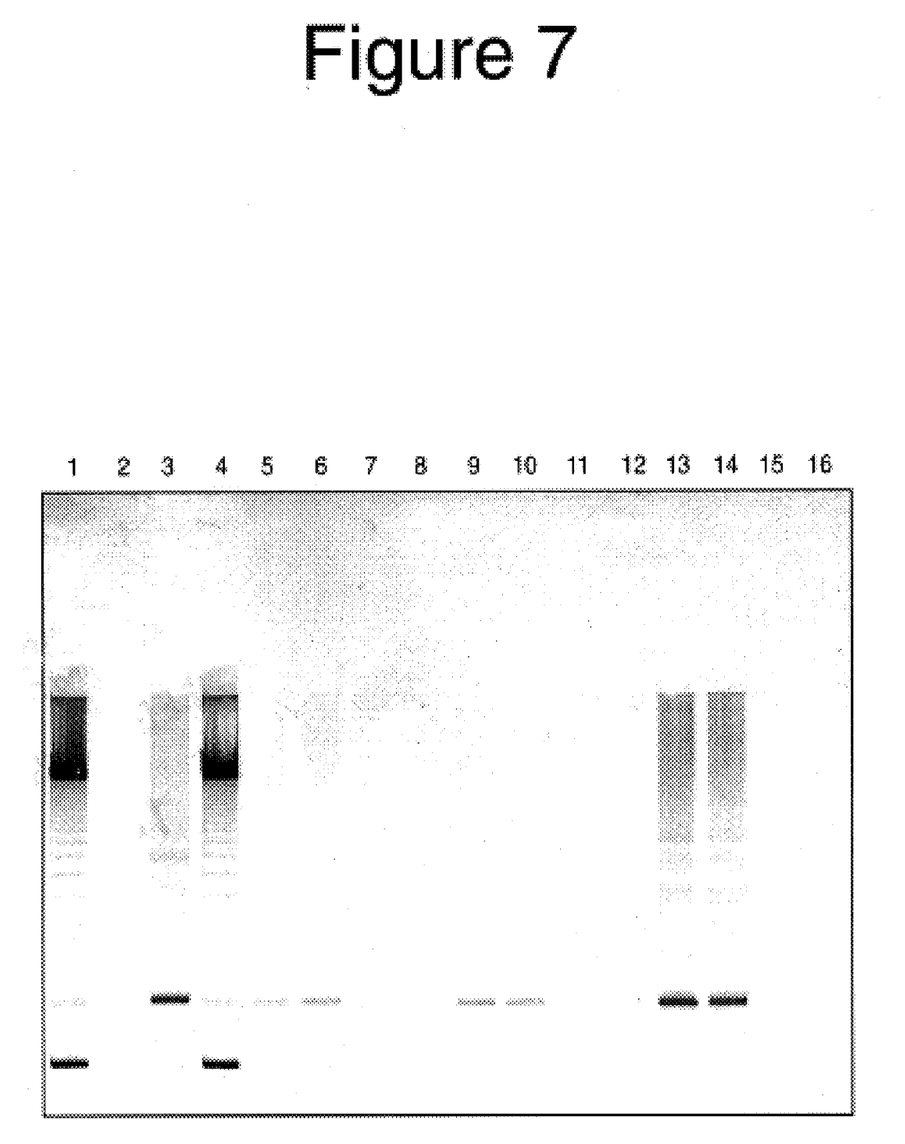
FIG. 7 is a view of an electrophoretic gel as described in Example 6.

Two separate one inch squares of 903, one treated and one untreated are exposed to blood collected in heparinized, citrate or EDTA containing blood collection tubes. The blood was allowed to dry. Two one eighth inch circles were hand punched from each. The circles were transferred to a 1.5 ml microcentrifuge tube containing 0.5 ml of water and vortexed for about 5 seconds. The circles were then processed as in Example 2 above to obtain template DNA for PCR. The amplified products were analyzed by electrophoresis on a polyacylamide gel which were visualized by silver staining. As shown in FIG. 7, the gel patterns demonstrated that PCR reactions using DNA templates from samples collected on untreated 903 paper generated little detectable PCR product, while those from samples collected on the present invention yielded a strong band indicating a successful PCR reaction. The lanes in FIG. 7 can be differentiated as follows: lanes 1 and 4 used a BRL 123 base pair ladder; lane 2 is a negative control (no template); lane 3 is a positive control (20 nanograms K562 genomic DNA); lanes 5 and 6 used human blood collected in potassium EDTA vacutainer and untreated 903 paper; lanes 9 and 10 used human blood collected sodium EDTA vacutainer and treated 903 paper; lanes 11 and 12 used human blood collected in sodium EDTA vacutainer and spotted onto untreated 903 paper; lanes 13 and 14 used human blood collected in sodium heparin vacutainer and spotted onto treated 903 paper; and lanes 15 and 16 used human blood collected in sodium heparin vacutainer spotted onto untreated 903 paper.

The ordinarily skilled artisan can appreciate that the present invention can incorporate any number of the preferred features described above. All publications or unpublished patent applications mentioned herein are hereby incorporated by reference thereto. Other embodiments of the present invention are not presented here which are obvious to those of ordinary skill in the art, now or during the term of any patent issuing from this patent specification, and thus, are within the spirit and scope of the present invention.

We claim:

1. A method for collecting and storing nucleic acids from a whole blood source having naturally occurring nucleic acid amplification inhibitors and an added blood stabilization agent selected from the group consisting of EDTA, heparin and citrate, comprising:

a) contacting said whole blood source with an adsorbent material that does not bind to nucleic acids and which has a chaotropic salt impregnated about the adsorbent material; and b) allowing the treated whole blood source to be absorbed onto or dried on the absorbent material for storage.

2. The method of claim 1 wherein the absorbent material comprises cellulosics, woven porous polymers, or non-woven porous polymers.

3. The method of claim 1 wherein the chaotropic salt comprises an iodide salt or a guanidinium salt.

4. The method of claim 3 wherein the guanidinium salt comprises guanidine hydrochloride, guanidine isothiocyanate, or guanidine thiocyanate.

5. A method for collecting, storing, and purifying nucleic acids from a whole blood source having naturally occurring nucleic acid amplification inhibitors and an added blood stabilization agent selected from the group consisting of EDTA, heparin and citrate, comprising:

a) contacting said whole blood source with an adsorbent material that does not bind to nucleic acids and which has a chaotropic salt impregnated about the adsorbent material, b) allowing said treated whole blood source to be absorbed onto or dried on the absorbent material for storage; and c) eluting the nucleic acids from said dried whole blood source into a solution that can be used in a nucleic acid amplification process.

6. The method of claim 5 wherein the absorbent material comprises cellulosics, woven porous polymers, or non-woven porous polymers.

7. The method of claim 5 wherein the chaotropic salt comprises an iodide salt or a guanidinium salt.

8. The method of claim 7 wherein the guanidinium salt comprises guanidine hydrochloride, guanidine isothiocyanate, or guanidine thiocyanate.

9. A method for collecting, storing, and purifying nucleic acids from a whole blood source having naturally occurring nucleic acid amplification inhibitors and an added blood stabilization agent selected from the group consisting of EDTA, heparin and citrate, comprising:

a) contacting said whole blood source with an adsorbent material that does not bind to nucleic acids and which has a chaotropic salt impregnated about the adsorbent material, b) allowing said treated whole blood source to be absorbed onto or dried on the absorbent material for storage; and c) adding the adsorbent material into a nucleic acid re-solubilizing solution.

10. The method of claim 9 wherein the absorbent material comprises cellulosics, woven porous polymers, or non-woven porous polymers.

11. The method of claim 9 wherein the chaotropic salt comprises an iodide salt or a guanidinium salt.

12. The method of claim 11 wherein the guanidinium salt comprises guanidine hydrochloride, guanidine isothiocyanate, or guanidine thiocyanate.

* * * * *